United States Patent [19]

Andersch et al.

[11] Patent Number: 5,418,164
[45] Date of Patent: May 23, 1995

[54] SELF-SUPPORTING CARRIER-FREE CELL GRANULATES FOR COMBATING PESTS AND TREATING PLANTS

[75] Inventors: Wolfram Andersch, Cologne; Jürgen Hartwig; Bernhard Homeyer, both of Leverkusen; Klaus Stenzel, Duesseldorf, all of Germany

[73] Assignee: Bayer Aktiengesellschaft, Leverkusen, Germany

[21] Appl. No.: 42,893

[22] Filed: Apr. 5, 1993

Related U.S. Application Data

[63] Continuation of Ser. No. 730,159, Jul. 15, 1991, abandoned, which is a continuation of Ser. No. 463,927, Jan. 8, 1990, abandoned, which is a continuation of Ser. No. 119,751, Nov. 12, 1987, abandoned.

[30] Foreign Application Priority Data

Nov. 20, 1986 [DE] Germany ............... 36 39 504.8

[51] Int. Cl.[6] ............... A01N 63/04; C12N 1/14; C12N 3/00; C12N 1/02
[52] U.S. Cl. ............... 435/254.1; 424/93.5; 435/261; 435/911
[58] Field of Search ............... 424/93 Q, 93.5; 435/254.1, 261, 911

[56] References Cited

U.S. PATENT DOCUMENTS 4,530,834 7/1985 McCabe et al. ............... 424/93.5
4,668,512 5/1987 Lewis et al. ............... 424/93.5
4,751,082 6/1988 Schaerffenberg et al. ........ 424/93.5

FOREIGN PATENT DOCUMENTS 0134873 9/1983 European Pat. Off. .
0145197 6/1985 European Pat. Off. .
0159891 10/1985 European Pat. Off. .
0268177 5/1988 European Pat. Off. .
2611801 9/1976 Germany .
2617892 12/1976 Germany .

OTHER PUBLICATIONS

"Biological Pesticides: Fungi to the Rescue," *Research: The Bayer Scientific Magazine*, 1989, pp. 22–31.
Tedders, W. L. et al. Environ. Entomol. 11(4):901–904, 1982.
ATCC Catalog of Fungi/Yeasts, 17th Ed. p. 212, 1987.
The American Heritage Dictionary, (1982), p. 572.
Commonwealth Agricultural Bureau, 1983, Abstract No. 83890397.
Commonwealth Agricultural Bureau, 1983, Abstract No. 71197346.

*Primary Examiner*—Jacqueline Stone
*Assistant Examiner*—Johnny F. Railey, II
*Attorney, Agent, or Firm*—Sprung Horn Kramer & Woods

[57] ABSTRACT

An agent for combating pests and for protecting plants comprising a carrier-free cell granulate of a microorganism which is suitable for combating pests or for plant treatment such as fungi or bacteria which are capable of mycelium formation, e.g. Deuteromycetes and Metarhizium including the new anisopliae strains DMS 3884 and 3885.

34 Claims, No Drawings ns, a process for their preparation and their use, as well as new microorganism strains.
SELF-SUPPORTING CARRIER-FREE CELL GRANULATES FOR COMBATING PESTS AND TREATING PLANTS This application is a continuation of application Ser. No. 730,159, filed Jul. 15, 1991, now abandoned, which is a continuation of application Ser. No. 463,927, filed Jan. 8, 1990, now abandoned, which is a continuation of application Ser. No. 119,751, filed Nov. 12, 1987, now abandoned.

The present invention relates to new agents for combating pests and plant treatment agents which consist of carrier-free cell granulates of microorganisms or contain at least one carrier-free cell granulate of microorganisms, a process for their preparation and their use, as well as new microorganism strains.

It has already been disclosed that certain microorganisms (bacteria, fungi and viruses) can be pathogenic towards pests, such as insects or nematodes, and can be used in combating pests. However, provision of suitable microorganism preparations (formulations) with a standardized efficacy in many cases meets with great difficulties, because the formulation of the microorganisms frequently has an adverse influence on their efficacy and storage stability.

New agents for combating pests and plant treatment agents have now been found and are characterized in that they consist of carrier-free cell granulates of microorganisms which are suitable for combating pests or plant treatment, or contain at least one carrier-free cell granulate of such microorganisms.

Agents for combating pests are to be understood as all agents according to the invention which can be used for combating undesirable animal and plant pests and nuisances (such as harmful arthropods and nematodes, broad-leaved weeds and graminaceous weeds, harmful bacteria and fungi). The efficacy of these agents for combating pests is in general based on the antagonistic ability (parasitization, toxin formation, competing properties) of the microorganisms used against the pests, which leads to their suppression or destruction. The agents for combating pests are preferably used in the sectors of agriculture, forestry, horticulture, housekeeping and hygiene, the preservation of stored products and the preservation of materials, in particular for preserving plants or harvested products. Preferred agents according to the invention for combating pests are those which can be used to combat pests which occur in the region of the soil.

Plant treatment agents are to be understood as all the agents according to the invention which are suitable for influencing or regulating the growth of plants (such as by exudation of plant hormones, provision of nutrients and the like). They can be used in particular in the sectors of agriculture, forestry and horticulture.

Preferred agents according to the invention are the agents for combating pests, preferably for combating animal pests (preferably arthropods and nematodes, in particular insects and nematodes, and especially preferably insects) and microbial pests (such as harmful bacteria and fungi), in particular animal pests.

The carrier-free cell granulates of microorganisms which are used according to the invention are essentially bead-shaped structures which are composed of microorganism cells fused like tissue and contain no carrier materials. Mechanically, they are so stable that they do not change adversely in an undesirable manner, for example by abrasion, during preparation, working up, bottling and use. The cell granulates preferably have diameters of 0.05 to 2.0 mm, preferably 0.1 to 1.5 mm and particularly preferably 0.5 to 1.0 mm.

Possible microorganisms which can be used according to the invention in the form of cell granulates are all microorganisms (bacteria and fungi) which have the capacity for mycelium formation. They must furthermore be able to form (under the conditions of the vacuum according to the invention) cell aggregations and cell granulates. If the cell granulates according to the invention are intended for combating pests, the microorganisms must be capable of impairing the vitality or reproductive capacity of the pests to be combated such that they can be adequately controlled on the basis of the action by the agents for combating pests. For this, the microorganisms which can be used according to the invention must be capable of releasing into the environment substances which have an appropriate action on the pests or be capable of parasitizing the pests to a sufficient degree.

If the cell granulates to be employed according to the invention are to be used as plant treatment agents, the microorganisms must be capable of releasing into the environment substances which act on the plants, for example phytohormones or nutrients, or which render substances which have an adverse influence on the plants harmless.

The microorganisms used in the cell granulates should not have pathogenic properties towards warm-blooded animals and moreover should not harm beneficial animals (for example earthworms or bees).

A large number of microorganisms are capable of forming cell granulates, and these are preferably of fungal species from the taxonomic classes of Phycomycetes, Ascomycetes, for example Chaetonium, Basidiomycetes and Deuteromycetes, in particular the representatives of fungi imperfecti, such as, for example, various species of Aspergillus, Alternaria, Aphanocladium, Beauveria, Coniothyrium, Colletotrichum, Meria (Drechmeria), Penicillium, Fusarium, Gliocladium, Pseudocercosporella, Trichoderma, Verticillium and Paecilomyces, and in particular also of Metarhizium and Gliocladium, particularly preferably of Metarhizium. Numerous strains of these fungi have an antagonistic activity against soil-borne phytopathogenic fungi, such as, for example, *Trichoderma hamatum* and *Gliocladium roseum*, against weeds, such as, for example, *Alternaria cassiae, Fusarium lateritum* and *Fusarium solani*, and against harmful insects, such as, for example, *Verticillium lecanii, Aspergillus parasiticus* and in particular *Metarhizium anisopliae*.

Of the microorganisms, fungicidal, nematopathogenic and ethomopathogenic microorganisms (in particular fungi of the Deuteromycetes class) are preferred. Nematopathogenic and entomopathogenic microorganisms are particularly preferred.

Especially preferred fungi are those of the genus Metarhizium, in particular of the species Metarhizium anisopliae, and amongst this species in particular the Metarhizium anisopliae strains P 0001 and P 0003, in particular strain P 0001. These new strains, which can be particularly advantageously used according to the invention and are the subject of the present invention, have been deposited in the Deutsche Sammlung von Mikroorganismen (German Collection of Microorganisms) (DSM), Grisebachstrasse 8, D-3400 Göttingen, Federal Republic of Germany, in agreement with the conditions of the Budapest Treaty on International Recognition of Deposit of Microorganisms for the purpose of patent proceedings on Oct. 24, 1986 and have the deposit numbers:

DSM 3884 (P 0001) and
DSM 3885 (P 0003).

The present invention also extends to the mutants and variants of these strains which have the essential features and properties for carrying out the invention. By the process according to the invention, these Metarhizium strains give cell granulates which have very favorable physical and biological properties which enable these cell granulates to be used as agents for combating pests, preferably for combating arthropods and nematodes, in particular insects and nematodes (especially insects) and especially preferably soil insects, that is to say insects which occur in the soil, on the soil or on plant material in the vicinity of the soil.

The present invention also relates to the new use of the abovementioned microorganisms, which are capable of mycelium formation, for producing the new agents for combating pests and plant treatment agents.

The new carrier-free cell granulates can contain nutrients (for example those which are used in fermentation in the preparation process according to the invention). These nutrients can promote a rapid growth of the microorganisms after use of the new agents.

They can also contain substances which have a protective action and prevent the microorganism cells from drying out too much (for example polyalcohols, such as sugars or glycerol).

To improve the storage stability, the new cell granulates can contain non-toxic antioxidant substances (such as ascorbic acid, 2,3-tert.-butyl-4-hydroxy-anisole, 2,6-di-tert.-butyl-p-cresol, propyl gallales or nordihydroguaiaretic acid).

Rapid rehydration after use can be achieved by the new cell granulates containing substances with a hygroscopic action (such as suitable polyalcohols, for example glycerol, sugars, oligo- and polysaccharides and their derivatives.

In a particular embodiment, the cell granulates according to the invention essentially contain an increased amount of permanent stages of microorganisms (i.e. resting or dormant stages, such as spores or conidia) on the surface. This in general results in a particularly long-lasting storage stability with a rapid multiplication and spread of the microorganisms applied in the form of the cell granulates.

In a particularly preferred embodiment, however, the cell granulates according to the invention contain none of the abovementioned additives at all. Cell granulates according to the invention which do not have an increased amount of permanent stages are preferred.

As well as the carrier-free cell granulates, the agents according to the invention can contain other agents for combating pests (for example fungicides, insecticides or herbicides) or plant treatment agents (for example fertilizers) in the form of admixtures.

Agents according to the invention which consist of carrier-free cell granulates (without further admixed substances) are preferred.

Compared with conventional microorganism formulations which have been proposed or used as agents for combating pests or plant treatment agents, the new cell granulates according to the invention have considerable advantages because of their physical and biological properties.

The cell granulates can easily be prepared by the process according to the invention. They can be separated off particularly easily in the production process. They are easy to handle during working (separation, drying, bottling, storage) and use, since they do not form a dust, have a defined particle size and very good pouring properties and can be very easily dosed and simply applied. Apart from a good mechanical stability, the new cell granulates have a high storage stability, so that they still display their complete biological action even after prolonged storage and the action standard determined at the production is thus retained, which is of particular importance in practice for pest-combating agents containing biological materials.

It has furthermore been found that the new agents for combating pests and plant treatment agents which consist of carrier-free cell granulates of microorganisms which are suitable for combating pests or plant treatment or contain at least one carrier-free cell granulate of such microorganisms are obtained by a process in which (A) to initiate the cell aggregation (first process step)
  a) in the case of microorganism cells with an essentially hydrophobic cell surface, after addition of one or more detergents to an aqueous slurry of the microorganisms which are suitable for combating pests or plant treatment and are obtained in a preculture, the cells are suspended and the cell suspension is introduced into water or an aqueous nutrient medium, so that cell aggregation takes place, or
  b) in the case of microorganism cells without an essentially hydrophobic cell surface, by addition of acids or bases to a slurry, in water or an aqueous nutrient medium, of the microorganisms which are suitable for combating pests or plant treatment and are obtained in a preculture, the pH value is adjusted so that cell aggregation takes place, or
  c) flocculants are added to slurry or suspension, in water or a nutrient medium, the microorganisms which are suitable for combating pests or plant treatment and are obtained in a preculture, so that cell aggregation takes place, and subsequently (B) to form the cell granulates (second process step), the resulting cell aggregations are subjected to fermentation under aerobic conditions in a nutrient medium, which contains complexing substances if appropriate, and the cell granulates formed are separated off, and (C) if appropriate, to form an essentially increased amount of permanent stages of microorganisms on the surface of the cell granulates, the cell granulates separated off are subjected to incubation under the conditions of surface culture, and (D) the resulting cell granulates, if appropriate after addition of or treatment with nutrients, substances with a protective action, substances with an antioxidant action and/or substances which aid rehydration, are dried and if appropriate mixed with other agents for combating pests or plant treatment agents.

The process according to the invention for the preparation of the cell granulates essentially consists of two phases. In the first phase, cell aggregation is initiated, the special biochemical properties of the particular microorganism cells being utilized, and in the second phase the actual cell granulates are formed in a fermentation process.

A preculture (inoculum) of the microorganisms is first prepared by the customary methods of surface cultures or liquid cultures, for example as slant tubes, on nutrient agar plates, on carrier materials which can be utilized as a nutrient substrate or in shaking flasks with liquid media. The nutrient media described below for the fermentation, for example, can be used here.

Cell aggregation can be initiated by various methods. The particular method suitable can be easily determined with the aid of simple series experiments.

Thus, inorganic or organic flocculants, for example swelling clays, such as bentonite, montmorillonite and attapulgite, or starch, size, polyacrylamide, carboxymethylcellulose and polyethylene oxide, can be added to a slurry of the microorganisms in water or an aqueous nutrient solution in order to achieve cell aggregation.

In the case of microorganism cells with an essentially hydrophobic cell surface, preferably in the case of permanent stages of the microorganisms (spores or conidia), a detergent (or a mixture of detergents), for example polyoxyethylene derivatives of sorbitol anhydrides (such as Tween 80) is added to a slurry of the cells in water or a nutrient solution and the cells are suspended. A detergent concentration of 0.01 to 5.0% (weight/volume), in particular 0.1 to 1.0% (weight/volume) is preferably used, The suspension preferably contains $10^3$ to $10^9$ cells/ml, in particular $10^5$ to $10^7$ cells/ml. The cell suspension is introduced into an aqueous liquid nutrient medium, preferably by injection. The volumes of cell suspension and nutrient medium here are preferably in a ratio of at least 1:5, in particular 1:50 to 1:100. The dilution of the detergent leads to the desired aggregation of the microorganism cells.

In the case of microorganisms without an essentially hydrophobic cell surface, preferably in the case of vegetative cells, aggregation of the cells can be achieved by a procedure in which the positively and negatively charged molecular groups on the cell surface in a slurry or suspension of the cells in water or an aqueous nutrient medium are neutralized by appropriate adjustment of the pH value until the desired cell aggregation occurs. The adjustment of the pH value can be achieved by addition of organic or inorganic acids or bases (for example sulphuric acid, hydrochloric acid, phosphoric acid, acetic acid, sodium hydroxide solution or triethylamine). The particular pH value which is most favorable can easily be determined by simple series experiments.

The cell aggregations obtained in this first phase are used in the second phase in the production of the cell granulates.

The second phase of the process, the formation of the cell granulates, is characterized by the intensive increase in growth of the biomass of a cell aggregate in the course of fermentation. To obtain stable cell granulates, this fermentation is advantageously carried out such that development of an intensively branched, filamentuous cell growth occurs, whereupon the formation of a tissue-like cell association is promoted.

Culture of the microorganisms in this case takes place under aerobic conditions and can be carried out in accordance with the generally customary methods, such as using shaking cultures, for example as shaking flasks, or as submerse culture in aerated fermenters, for example in customary submerse fermentation tanks. Fermentation can be carried out by a discontinuous or continuous process, but preferably in discontinuous operation.

The cell granulates can be produced in a single-, two- or multi-stage process, but preferably in a single-stage process.

The preculture (inoculum) is obtained by the customary methods in surface cultures, for example as slant tubes, on nutrient agar plates or on carrier materials which can be utilized as a nutrient substrate, or in a liquid culture, such as, for example, in shaking flasks.

The fermentation process according to the invention is carried out in a liquid nutrient medium, preferably in aqueous-liquid nutrient media. Suitable nutrient media here are those with a composition which meets the specific nutrient requirements of the corresponding microorganism, such as, for example, *Metarhizium anisopliae*. The nutrient medium must contain one or more assimilable sources of carbon and nitrogen as well as mineral salts, and these products are used in the form of defined individual constituents or in the form of complex mixtures such as are used, in particular, as biological products of vegetable or animal origin. Possible sources of carbon are all the customary sources of carbon. Examples which may be mentioned are carbohydrates, in particular polysaccharides, such as starch or dextrins, disaccharides, such as maltose or sucrose, monosaccharides, such as glucose or xylose, and sugar-alcohols, such as mannitol or glycerol, and naturally occurring mixtures, such as malt extract, molasses or whey. Possible sources of nitrogen are all the customary organic and inorganic sources of nitrogen. Examples which may be mentioned are amino acids, proteins, protein hydrolysates, nucleoside bases and soy bean flour, cottonseed flour, lentil flour, pea flour, soluble and insoluble vegetable proteins, corn steep liquor, yeast extract, peptones and meat extract, as well as ammonium salts and nitrates, for example $NH_4Cl$, $(NH_4)_2SO_4$, $NaNO_3$ and $KNO_3$. The mineral salts which the nutrient medium should contain supply, for example, the following ions:

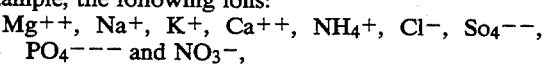

and ions of the customary trace elements, such as Cu, Fe, Mn, Mo, Zn, Co and Ni. If the sources of carbon or nitrogen or the water used do not contain a sufficient amount of these salts or trace elements, it is advantageous to supplement the nutrient medium appropriately. The composition of the nutrient media can be varied within wide limits. The nature and composition of the nutrient media will in general depend on what constituents each case particularly advantageously available. In general, the nutrient solutions contain preferably about 0.5 to 8%, in particular 0.6 to 6%, of sources of carbon, preferably about 0.5 to 4%, in particular 0.5 to 2%, of sources of nitrogen and preferably about 0.001 to 0.5%, in particular 0.003 to 0.3%, of mineral salts.

In carrying out the process, it may be advantageous to use only relatively low concentrations of the soluble nutrient solution constituents at the start of culture and then to top up the fermentation batch fractions in the course of the first culture phase by relatively frequent additions of these constituents in the form of sterile, relatively concentrated solutions.

To increase the stability of the granulates, it may prove to be advantageous to add complexing substances to the nutrient medium. Suitable complexing substances are inorganic and organic chelating compounds, such as, for example, ethylenediaminetetraacetate, diaminocyclohexane-N,N-tetraacetate, diethylenetriaminepentaacetate, cyanides and citrates, with or without complexed metal ions. The complexing substances are preferably employed in a concentration of 0.5 to 10 mM, particularly preferably 1.0 to 5.0 mM.

The pH value of the growing culture should be kept within a range which guarantees initiation of cell aggregation and formation of granulates of sufficient stability with maximum cell growth. The expert can determine the optimum pH value range for cell aggregation and granulate production by customary methods (series experiments) in a simple manner. When carrying out the fermentation process, it may be advantageous to change the pH value as a function of the fermentation phase in order to promote maximum biomass production. Too great a drop of the pH value into the acid range can be compensated by additions of bases, for example NaOH or $CaCO_3$. As is customary in fermentation technology, automatic pH regulation can also be carried out, in which sterile organic or inorganic acids or alkalis are injected into the culture at intervals.

The oxygen supply to the growing culture is advantageously guaranteed in a manner such that the oxygen does not become the growth-limiting factor of the microorganisms. The oxygen supply to the cultures is usually effected by shaking, for example in shaking flasks, or by aeration in association with stirring of the fermentation tanks.

In the process according to the invention, the granulate diameter or granulate stability is controlled by choosing the speed of shaking or rotation of the culture flasks, the number of revolutions being kept preferably in a range of 50 rpm to 250 rpm, particularly preferably in a range of 100 to 200 rpm, depending on the granulate diameter or granulate stability. In the case of culture of the microorganisms in fermentation tanks, the stirring speed is preferably kept in a range of 30 to 800, in particular 50 to 500 rpm (rpm means revolutions per minute). The expert can easily determine the particular shaking or stirring speed which is most advantageous and leads to the formation of cell granulates with the desired diameter or stability by simple series experiments.

In carrying out the process, it may be advantageous to keep the shaking or stirring speed in a very low range at the start of culture and, after increased growth of the biomass has clearly started, to switch to a range of higher shaking or stirring speed.

The temperature for initiation of the cell aggregation or for preparation of the cell granulates is advantageously kept within a range which permits maximum cell growth, but preferably in a range of 10° to 30° C.

As is general with microbiological processes, foreign infections in the culture media should be avoided. The customary measures are taken here, such as sterilization of the nutrient media, of the culture vessels and of the air required for the aeration. Steam sterilization and dry sterilization, for example, can be used to sterilize the devices, the temperatures preferably being 100° to 140° C., in particular 120° to 130° C.

If an undesirable amount of foam is formed during culture, the customary chemical foam suppressants, for example liquid fats and oils, oil-in-water emulsions, paraffins, higher alcohols, such as octadecanol, silicone oils or polyoxyethylene or polyoxypropylene compounds (for example in amounts of up to about 1%), can be added. Foam can also be suppressed or eliminated with the aid of the customary mechanical devices (which utilize, for example, centrifugal forces).

The end of the fermentation is determined by the production of the biomass. The culture is advantageously interrupted before or at the time of maximum biomass production for reasons of stability of the granulates or of maintaining the vitality of the cells in the granulates. The time for the end of production can easily be specified by the expert using the customary methods of biomass determination. The industrial production process can be controlled by fermentation-specific characteristic data which can be determined in a simple manner, such as pH value, partial pressure of oxygen, partial pressure of carbon dioxide or concentration of assimilable nutrient constituents.

The cell granulates can be separated off from the nutrient medium in the customary manner, for example by filtration over a sieve or sieve-like fabrics of appropriate pore width, or by filtration, centrifugation or separation. To avoid contamination of the cell granulates by undesirable microorganisms which could cause a reduction in quality or destruction of the product due to their metabolic activities, the cell granulates are advantageously concentrated (and if appropriate also further processed) under sterile conditions, such as, for example, in sterilized separators.

For easier further processing of the cell granulates, it may be advantageous to add to the biomass to be concentrated the materials which are usually used and which prevent lumping of the cell granulates during the concentration process. Materials which are suitable for this are those which neutralize the surface, such as, for example, the clay-like materials bentonites, talc, pyrophylites, celite, lime, kaolin, attapulgite or other synthetic silicates.

The cell granulates are dried by dehydration of the microorganisms. The customary methods for drying the biomass by means of heat transfer by convection, such as, for example, current and fluidized bed drying, or by means of heat transfer by contact, such as, for example, the processes of plate, paddle, tumble, belt, roller, vacuum chamber and vacuum freeze drying, can be used here. The drying process can also consist of a combination of two or more of these processes. The cell granulates are dehydrated in a discontinuous or continuous process, but preferably in a discontinuous process. Specifically, the processes are designed so that the vitality of the cells in the granulates is guaranteed for the longest possible period of time. It should furthermore be ensured during drying of the cell granulates that the mechanical stress on the cell granulates is kept as low as possible.

The dried product should have a water content of 0 to 30% (weight/weight), but preferably of 2.5 to 15% (weight/weight). The water content (based on a product dried at 100° C. for 12 hours) is determined by the customary methods.

To protect the cells in the granulates from damage such as may occur during the drying process as a result of a reduction in temperature or increase in temperature or from dehydration which is too intense, it may be advantageous to pretreat the granulates with appropriate protective substances before drying. Substances which are suitable here are the organic or inorganic substances which are known for this intended use and achieve a protective action in a defined form or as a complex mixture, for example polyalcohols, such as sugars or glycerol. The treatment of the cells is carried out by the customary methods by immersion, washing, spraying or mixing of the cell granulates with the protective agents.

Protection of the cells in the granulates from uncontrolled oxidation reactions can be achieved by treatment of the not yet dried cell granulates with non-toxic antioxidant substances, such as, for example, ascorbic acid, 2,3-tert.-butyl-4-hydroxy-anisole, 2,6-di-tert.-butyl-p-cresol, propyl gallates or nordihydroguaiaretic acid. Treatment is carried out with the aid of customary methods, by immersing, washing, spraying or mixing the granulates with the protective agents.

To develop the biological activity when combating pests, the cell granulates can also be treated, before drying, with materials which aid rehydration of the cells. Materials which are suitable for this are all the non-toxic hygroscopic materials, in particular polyalcohols, such as glycerol, sugars, sugar polymers or derivatives of sugar polymers.

To activate and intensify the biological action, especially in combating pests, it may be advantageous for the cell granulates to be treated, before drying, with nutrients which aid rapid multiplication of the microorganisms and thus a denser population of the site of action. Suitable nutrient-like substances are all the assimilable sources of carbon and nitrogen such as can also be used for culture or during fermentation of the corresponding microorganism.

To maintain a long vitality of the microorganisms and to achieve a particularly good storage stability of the cell granulates, it may be advantageous to induce the formation of permanent stages, such as, for example, conidia, on the surface of the cell granulates, especially fungi with thread-like cell growth, such as, for example, *Metarhizium anisopliae*, before the cell granulates are dried. The permanent stages are formed by subjecting the cell granulates obtained by fermentation to additional incubation under conditions of surface cultures, for example on flat dishes, troughs or sheets. The atmospheric humidity is thereby kept in a range from 100% to 40% relative atmospheric humidity, but preferably in a range from 100% to 80% relative atmospheric humidity, by customary methods. The incubation should be carried out at temperatures of not less than 10° C. and not more than 30° C., but preferably in a range from 20° to 27° C. The formation of the permanent stages can be monitored in the simplest manner by the pigmentation of the cell granulates or by customary methods of microscopy.

For uniform formation of the permanent stages on the surface of the cell granulates, it may prove to be advantageous to agitate the cell granulates mechanically, such as, for example, by shaking, at certain intervals of time.

To intensify the formation of permanent stages, it may prove to be advantageous to treat the cell granulates, before the incubation in surface cultures, with carbon- or, in particular, nitrogen-containing nutrients, such as sugars, amino acids, for example tryptophan, glutamate, histidine or aspartate, or protein-containing materials. The nutrients are employed in a defined form or as complex mixtures, the optimum concentrations being determined by the customary methods. The treatment is carried out by the customary methods, by immersing, washing or spraying the not yet dried cell granulates.

The incubation of the cell granulates to form permanent stages is advantageously carried out under sterile conditions, such as, for example, in sterilized containers, to avoid contamination by undesirable microorganisms.

Cell granulates loaded with permanent stages in this way are preserved, as described above, by dehydration of the microorganisms. It is advantageous here to ensure that the mechanical stress on the cell granulates is kept as low as possible in order to avoid removal of the permanent stages. Under these prerequisites, the methods of heat transfer by contact processes, such as, for example, the processes of belt, roller, vacuum chamber and vacuum freeze drying, are primarily suitable for the drying operation.

The cell granulates according to the invention are stored in closed containers under dry conditions, temperatures between 0° and 250° C. To maintain the vitality of the cells in the granulates, it may be advantageous to store the granulates with exclusion of oxygen, such as, for example, by storage under an atmosphere of nitrogen, carbon dioxide or other inert gases, or of gas mixtures of the gases mentioned, and furthermore the exclusion of oxygen can be achieved by packaging the cell granulates under conditions of decreased pressure.

The agents, according to the invention, for combating pests can be employed, when appropriate microorganisms are used, for combating animal pests, preferably arthropods and nematodes, in particular insects and arachnids, which occur in agriculture, in forests, in horticulture, in the preservation of stored products and materials and in the hygiene sector.

They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec.* From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria* migratorioides, *Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp.

From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Hellothis spp., *Spodoptera exigua Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes sppo, Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The new agents for combating pests are preferably used for combating insects and nematodes, preferably insects which occur in or on the soil (or in the vicinity of the soil) (soil insects).

The agents for combating insect pests can also be employed in traps, if appropriate after admixing with baits or lacquer substances.

The agents, according to the invention, for combating pests can be employed, if appropriate microorganisms are used, for combating harmful microbes (fungi and bacteria).

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Pseudomonas species, such as, for example, *Pseudomonas solanacearum;*

Pythium species, such as, for example, *Pythium ultimum;*

Phytophthora species, such as, for example, *Phytophthora cactorum;*

Fusarium species, such as, for example, *Fusarium oxysporum;*

Botrytis species, such as, for example, *Botrytis cinerea;*

Pseudocercosporella species, such as, for example, *Pseudocercosporella herpotrichoides;*

Rhizoctonia species, such as, for example, *Rhizoctonia solani;*

Sclerotium species, such as, for example, *Sclerotium rolfsii;*

Sclerotinia species, such as, for example, *Sclerotinia sclerotirum;*

Verticillium species, such as, for example, *Verticillium alboatrum;*

Phialophora species, such as, for example, *Phialophora cinerescens;*

Phomopsis species, such as, for example, Phomopsis sclerotioides.

The agents, according to the invention, for combating pests (or plant treatment agents) can also be used, if suitable microorganisms are employed, as defoliants, desiccants, agents for destroying broad-leaved weeds and, especially, as weedkillers. By weeds, in the broadest sense, there are to be understood all plants which grow in locations where they are undesired. The selectivity of the herbicides depends essentially on the amount used.

The agents according to the invention can be used, for example, on the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the agents according to the invention is in no way restricted to these genera, but also extends in the same manner to other plants.

The agents are suitable, depending on the concentration, for the combating of weeds, for example on industrial terrain and rail tracks, and on paths and squares with or without tree plantings, likewise for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The agents according to the invention can be used as such or also in their formulations (preferably as such) as a mixture with other known agents for combating pests, such as insecticides, acaricides, nematicides, bird repellants, plant nutrients, herbicides and agents for improving soil structure.

The agents according to the invention are applied in the customary manner, preferably by scattering. The agents according to the invention are particularly preferably applied without another formulation, application preferably being by scattering.

The amount of the agents applied can vary within a relatively wide range. It essentially depends on the nature of the desired effect and on the nature of the microorganisms employed. In the agriculture, forestry and horticulture sectors, the application amounts are in general between 0.1 and 50 kg of agent per hectare of soil surface, preferably between 1 and 25 kg per ha.

The agents, according to the invention, for combating pests are preferably used for soil treatment. Pests which occur in the area of the soil are preferably combated here.

The present invention may be illustrated by the following examples.

Note the strains identified by a "CBS No." were obtained from the Sammlung des Centraalbureau voor Schimmelcultures (Collection of the Central Bureau for Mould Cultures) (CBS), Oosterstraat 1, NL-3740 AG Baarn, Netherlands.

A) Preparation of the cell granulates using the example of *Metarhizium anisopliae* P 0001 (DSM 3884)
1. 10.0 liter fermentation for the preparation of cell granulates

*Metarhizium anisopliae* P 0001 (DSM 3884) is kept as a stock culture on slant tubes with malt extract-glucose-peptone nutrient agar (malt extract 20.0 g; glucose 20.0 g; peptone 1.0 g; agar 15.0 g, water to 1,000 ml, pH 7.5). The slant tubes are stored in a refrigerator at 4° C.

Conidia of the *Metarhizium anisopliae* strain are obtained as an inoculum, for the fermenter cultures, on malt extract-glucose-peptone-agar plates, which are seeded with a conidia suspension from slant tubes and incubated of 25° C. for 15 to 16 days.

The precultures for the fermentations are grown in 1.0 liter conical flasks filled with 100 ml of nutrient solution. The nutrient solution has the following composition:

| Glucose | 10.0 g |
|---|---|
| Yeast autolysate (Ohly) | 10.0 g |
| $KH_2PO_4$ | 1.74 g |
| Fe-III citrate | 0.28 g |
| $MnSO_4 \times H_2O$ | 0.031 g |
| $ZnSO_4 \times 7 H_2O$ | 0.009 g |
| $CuSO_4 \times 5 H_2O$ | 0.0057 g |
| $MgCl_2 \times 6 H_2O$ | 0.406 g |
| $H_2O$ to 1,000 milliliters, pH 7.5. | |

To avoid foaming, a silicone oil (Baysilone E, trademark of Bayer AG, Leverkusen, Federal Republic of Germany) (30%, volume/volume; 0.5 ml/l of nutrient solution) is added to the nutrient medium. The nutrient solution is seeded with a conidia suspension which has been obtained by skimming malt extract-glucose-peptone-agar plates with an aqueous solution (1.0%, volume/volume) of a non-ionic surface-active agent (polyoxyethylene derivative of sorbitol anhydride, Tween 20) (trademark of ICI America Inc. USA). The conidia titre in the precultures is $10^6$ conidia per milliliter of nutrient solution. After seeding, the cultures are incubated for 24 hours on a rotary shaker at 100 revolutions per minute at a temperature of 25° C.

The cell granulates are prepared in a 15.0 liter fermenter which contains 10.0 liter of the abovementioned nutrient solution. The nutrient medium was sterilized at 121° C. for 45 minutes.

The fermenters are seeded with 3.0%, volume/volume, of preculture. The following culture conditions are maintained during the fermentation:

| Temperature | 25° C. |
|---|---|
| Stirring speed | 400 revolutions per minute |
| Rate of aeration | 5 liter of air per minute |

The fermentations are ended after 60 to 80 hours.

2. Drying of the cell granulates

The *Metarhizium anisopliae* cell granulates obtained by the fermentation described above are separated off from the fermentation broth by sieving over a fabric of plastic with a pore diameter of 0.1 mm. An additional content of non-bonded fermentation liquid is separated off by filtration of the cell granulates by suction over a suction filter connected to a membrane pump.

The cell granulates are dried in a fluidized bed granulator with a filling volume of 16.5 liters. The cell granulates are introduced into the fluidized bed granulator in portions of 200 g each and are dried in a current of air at a flow rate of 1,300 liter per minute. The temperature of the air fed in is 40° C. The drying process is monitored by regular determination of the water content of the cell granulates. At a water content of the cell granulates of 10% (weight/weight, based on a product dried at 100° C. for 12 hours), the drying process is ended.

The cell granulates are stored under dry conditions at room temperature.

B) Preparation of cell granulates with conidia formation on the granulate surface using the example of *Metarhizium anisopliae* P 0001 (DSM 3884)

The cell granulates are prepared and worked up as described under Example A). After the fermentation broth has been separated off, the cell granulates are washed with a concentrated glucose solution (10%, weight/volume; 100 ml of glucose solution for 50 g of moist cell granulates). The non-bonded glucose solution is then filtered off with suction over a suction filter.

The cell granulates thus treated are incubated for 60 to 70 hours in a humidity chamber, relative atmospheric humidity 100%, at a temperature of 25° C. The formation of conidia on the surface of the granulates can be monitored via the intensity of the green pigmentation.

C) 10.0 liter fermentation for preparation of cell granulates using the example of *Gliocladium roseum* (CBS 595.75)

In the case of *Gliocladium roseum* (CBS 595.75), the strain is kept and the conidia are obtained as an inoculum for the precultures by the process described in Example 1 for *Metarhizium anisopliae* P 0001.

The precultures for the fermenter cultures are grown in 1.0 liter conical flasks filled with 100 millilitres of nutrient solution. The nutrient solution has the following composition:

| Glucose | 10.0 g |
|---|---|
| Yeast extract | 10.0 g |
| H₂O to 1,000 milliliters, pH 6.0 | |

The precultures are seeded with a conidia suspension which has been obtained by flotation of agar plate cultures (malt extract-glucose-peptone-agar). The conidia titre in the precultures is $10^6$ conidia per milliliter of nutrient solution. After seeding, the cultures are incubated for 24 hours on a rotary shaker at 150 revolutions per minute and a temperature of 25° C.

The cell granulates are prepared in a 15.0 l fermenter filled with 10.0 l of nutrient solution of the following composition:

| Starch | 10.0 g |
|---|---|
| Casein hydrolysate | 10.0 g |
| H₂O to 1,000 milliliters, pH 6.0 | |

The nutrient medium is sterilized at 121° C. for 45 minutes. The fermenters are seeded with 1.5%, volume/volume, of preculture. The following parameters are maintained during the fermentation:

| Temperature: | 25° C. |
|---|---|

-continued

| Aeration values: | 5.0 l of air per minute |
|---|---|
| Stirring speed: | 100 rpm for 24 hours after inoculation |
| | 200 rpm from the 24th hour to the end of fermentation |

The fermentations are ended after 60 to 80 hours.

D) Production of cell granulates of various microorganisms in shaking cultures

Cell granulates can be formed by establishing certain boundary conditions, which have been determined in series experiments, in shaking cultures. Microorganisms, in particular the representatives of the Deuteromycetes, which are known to have a biological activity in combating pests were chosen as examples.

The strain is kept and the conidia for the inoculum of the shaking cultures are obtained by the process described for *Metarhizium anisopliae* P 0001 (Example 1).

The cell granulates are formed in conical flasks with a total volume of 1.0 l, each of which are filled with 100 milliliters of the stated nutrient solution. The culture batch is autoclaved at 121° C. for 20 minutes.

The culture batches are seeded with a conidia suspension obtained by flotation of agar plate cultures. After the seeding, the conidia titre is $10^6$ conidia per milliliter of nutrient solution. After seeding, incubation is carried out on a notary shaker with an amplitude of 5.0 cm; the shaking speed (revolutions per minute) is shown in the table. The temperature is kept constant at 25° C.

The conditions under which the various microorganisms are induced to form cell granulates are shown by way of example in Table 1.

TABLE 1

| Boundary conditions for the formation of cell granulates of various microorganisms | | | | |
|---|---|---|---|---|
| Microorganism | Indication | Nutrient medium | pH value | Shaking speed |
| *Gliocladium viride* (CBS 137.79) | Fungicide | Standard 1* | 7.5 | 100 rpm |
| *Aphanocladium album* (CBS 376.77) | Fungicide | Standard 1** | 6.0 | 50 rpm |
| *Gliocladium solani* (CBS 227.80) | Fungicide | Standard 1 | 7.5 | 50 rpm |
| *Gliocladium virens* (CBS 344.47) | Fungicide | Standard 2 | 7.5 | 100 rpm |
| *Coniothyrium minitans* (CBS 641.80) | Fungicide | Standard 2 | 7.5 | 100 rpm |
| *Meria coniospora* (= *Drechmeria coniospora*) (CBS 615.82) | Nematicide | Standard 2 | 7.5 | 100 rpm |
| *Verticillium Lecanii* (CBS 318.70 C) | Insecticide | Dextrin, 1.0% w/v Casein, 1.0% w/v | 4.0 | 75 rpm |
| *Verticillum bulbillosum* (CBS 571.78) | Fungicide | Standard 1 | 7.5 | 100 rpm |
| *Penicillium expansum* (CBS 481.84) | Fungicide | Standard 1 | 7.5 | 100 rpm |
| *Penicillum oxalium* (CBS 460.67) | Fungicide | Standard 2 | 7.5 | 100 rpm |
| *Colletotrichum gloeosporioides* (CBS 796.72) | Herbicide | 1% of casein in 1% of glucose water | 7.0 | 100 rpm |

Note:
*Standard medium 1: Potato infusion of 200 g of Potatoes; glucose 20.0 g, water to 1,000 ml
**Standard medium 2: Composition see Example 1 for Metarhizium anisopliae P 0001

The biological efficacy of the cell granulates according to the invention may be illustrated by the following examples:

Example 1

| Test insect: | *Agrotis segetum*, larvae in the 3rd stage |
|---|---|
| Test cell granulate: | Cell granulate of *Metarhizium anisopliae* according to Example A with a particle size |

-continued of 0.5 to 1.0 mm (diameter)

The cell granulate is mixed intimately with field soil (water content: 15% by volume). The concentration of the cell granulate in the soil is given here as weight of granulate per volume unit of soil (ppm=mg/l).

Paraffinated paper pots are filled with soil treated with the cell granulate, the test insects are immediately introduced into the soil and the experimental pots are closed and placed at a temperature of 20° C. throughout the duration of the experiment. During the experimental procedure, carrot slices are available ad libitum as a source of food for the test insects. After 10 to 20 days, the effectiveness of the cell granulate is determined in % (Abbott) by counting the dead and living test insects. The effectiveness is 100% if all the test insects have been destroyed, and it is 0% if just as many test insects are still alive as in the control.

| Result: Concentration of the cell granulate in ppm | Effectiveness in % |
|---|---|
| 10,000 | 100 |

Example 2

| Test insect: | Diabrotica balteata, larvae in the 2nd stage |
|---|---|
| Test cell granulate: | Cell granulate of Metarhizium anisopliae P 0001 with a particle size of 1.0 mm (diameter) |

The cell granulate is mixed intimately with field soil (water content: 15% by volume). The concentration of the cell granulate in the soil is given here as weight of granulate per volume unit of soil (ppm=mg/l).

Paraffinated paper pots are filled with soil treated with the cell granulate and the test insects are introduced immediately into the soil. Pregerminated corn seed is also sown in the treated soil as a source of food for the test insects. The experimental pots are closed and are placed at a temperature of 20° C. throughout the duration of the experiment. After 10 to 20 days, the effectiveness of the cell granulate is determined in % (Abbott) by counting the dead and living test insects. The effectiveness is 100% if all the test insects have been destroyed, and it is 0% if just as many test insects are still alive as in the control.

| Result: Concentration of the cell granulate in ppm | Effectiveness in % |
|---|---|
| 10,000 | 100 |

Example 3

| Test insect: | Tenebrio molitor, larvae in the 3rd stage |
|---|---|
| Test cell granulate: | Cell granulate of Metarhizium anisopliae according to Example A with a particle size of 0.5 to 1.0 mm (diameter) |

The cell granulate is mixed intimately with field soil (water content: 12% by volume). The concentration of the cell granulate in the soil is given here as weight of granulate per unit volume of soil (ppm=mg/l).

Paraffinated paper pots are filled with soil treated with the cell granulate, the test insects are introduced immediately into the soil and the experimental pots are closed and placed at a temperature of 20° C. throughout the duration of the experiment. After 10 days, the effectiveness of the cell granulate is determined in % (Abbott) by counting the dead and living test insects. The effectiveness 100% if all the test insects have been destroyed, and it is 0% if just as many test insects are still alive as in the control.

| Result: Concentration of the cell granulate in ppm | Effectiveness in % |
|---|---|
| 5,000 | 100 |

Example 4

| Test pathogen: | Fusarium culmorum |
|---|---|
| Test plant: | Triticum aestivum cv. Vuka |
| Test cell granulate: | Cell granulate of Aphanocladium album CBS 276.77 or Verticillium bulbillosum CBS 571.78 according to Example D with a particle size of 0.5–1.0 mm |

Plastic dishes are filled with greenhouse standard soil (Balster, D-5758 Fröndenberg) and the soil is infested with the pathogen by spraying a spore suspension of Fusarium culmorum. Wheat seed is sown on this soil. During sowing, the cell granulates are distributed by broadcasting onto the soil and the dishes are then covered with soil and watered. During the experimental procedure, the dishes are kept in a greenhouse at 20° to 22° C. and supplied with water as required.

After 2 to 4 weeks, the effectiveness in % (Abbott) is determined by counting the healthy and diseased plants. The effectiveness is 100 if all the plants are healthy, and it is 0 if the same number of plants are diseased as in the control.

| Result Amount of cell granulate applied in g/m$^2$ | Effectiveness (% Abbott) | |
|---|---|---|
| | *A. album* | *V. bulbillosum* |
| 30 | 83 | 73 |

Example 5

| | |
|---|---|
| Test pathogen: | *Rhizoctonia solani* |
| Test plant: | *Pisum sativum* cv. Wunder von Kelvedon |
| Test cell granulate: | Cell granulate of *Aphanocladium album* CBS 376.77 according to Example D with a particle size of 0.5–1.0 mm |

Pea seeds are sown on greenhouse standard soil (Balster, D-5758 Fröndenberg) introduced into plastic dishes. During sowing, the cell granulates are distributed on the soil by broadcasting. The dishes are then covered with soil infested with the pathogen. After watering, the experiment is kept in a greenhouse at 20° to 22° C. and supplied with water as required.

After 2 to 4 weeks, the effectiveness in % (Abbott) is determined by counting the healthy and diseased plants.

The effectiveness is 100 if all the plants are healthy, and it is 0 if the plants are diseased to the same degree as in the control.

| Result Amount of cell granulate applied in g/m² | Effectiveness (% Abbott) |
|---|---|
| 30 | 59 |

Example 6

| Test pathogen: | *Fusarium oxysporum* f. sp. *lycopersici* |
|---|---|
| Test plant: | *Lycopersicon esculentum* cv. *Fremdgens Rheinlands Ruhm* |
| Test cell granulate: | Cell granulate of *Gliocladium roseum* CBS 579.75 according to Example C) with a particle size of 0.5 to 1.0 mm |

Plastic pots are filled with greenhouse standard soil (Balster, D-5758 Frondenberg) and a plant hole is formed with a dibber. Before planting, conidia of the pathogen are introduced in an aqueous suspension into the soil. The cell granulates of *G. roseum* are distributed in the plant holes and tomato seedlings 3 to 4 weeks old are then immediately planted and watered. During the experimental procedure, the plants are kept in a greenhouse at 20° to 22° C. and supplied with water as required.

After 3 to 4 weeks, the experiment is evaluated by
a) determining the plant growth in relation to the control free from infestation
b) evaluating the plant behavior on a scale of 0 to 5 (0=no symptoms, 5=plant died)
c) determination of the stem cross-section discolored brown in per cent. The last value is used to determine the effectiveness in % (Abbott). The effectiveness is 100 if no brown discolorations are to be detected; it is 0 if the extent of the brown discolorations corresponds to that of the untreated control.

| Result Concentration of the cell granulate in ppm (mg/l of soil) | % plant growth to the desease-free control | Rating (0–5) | Effectiveness (% Abbott) |
|---|---|---|---|
| 1.500 | 112 | 0 | 100 |

Description of the *Metarhizium anisopliae* strains P 0001 (DMS 3884) and P 0003 (DSM 3885)

The *Metarhizium anisopliae* strains P 0001 and P 0003 grow in the form of septa ted branched hypha strands. When grown on agar surfaces, the fungi develop a white, downy air mycelium.

After development of the air mycelium, the formation of the permanent stages, so-called conidia, starts, these having a length of 9.0 to 12.0 μm and a diameter of 2.0 to 3.0 μm. The conidia are arranged in uniform chains, several strands of chain as a rule lying side by side. The pigmentation of the conidia gives the colonies of *Metarhizium anisopliae* strain P 0001 (DSM 3884) a brown-green coloration when grown on oatmeal agar, and those of *Metarhizium anisopliae* strain P 0003 (DSM 3885) a yellow-brown coloration.

When grown in liquid cultures, in addition to the thread-like cell form (hypha), the fungi also develop yeast-like individual cell stages, so-called blastospores. The length of the blastospores is 22.0 to 25 μm and their diameter is 6.0 to 8.0 μm.

It will be understood that the specification and examples are illustrative but not limitative of the present invention and that other embodiments within the spirit and scope of the invention will suggest themselves to those skilled in the art.

What is claimed is:

1. Self-supporting carrier-free cell granulates consisting essentially only of cell aggregates of fungi of the class Deuteromycetes, said fungi being capable of mycelium formation, and said granulates having an essentially bead shaped structure and a diameter of about 0.1 to about 1.5 mm.

2. Self-supporting carrier-free cell granulates according to claim 1, which comprise granulates of fungi of the genus Metarhizium.

3. Self-supporting carrier-free cell granulates according to claim 2, which comprise granulates of fungi of *Metarhizium anisopliae* strain P 0001, which has the deposit number DSM 3884, or strain P 0003, which has the deposit number DSM 3885, or mutants of said strains having the essential features and properties of P 0001 or P 0003.

4. A method of combatting insects comprising applying to such insects or to an insect habitat an insecticidally effective amount of the self-supporting carrier-free granulates according to claim 1.

5. A method according to claim 4, wherein the self-supporting carrier-free granulates comprise fungi of the genus Metarhizium.

6. A method according to claim 5, wherein the self-supporting carrier-free granulates comprise fungi of *Metarhizium anisopliae* strain P 0001, which has the deposit number DSM 3884, or strain P 0003, which has the deposit number DSM 3885, or mutants of said strains having the essential features and properties of P 0001 or P 0003.

7. A composition comprising:
(a) self-supporting carrier-free granules according to claim 1; in admixture with:
(b) fungicides, insecticides, herbicides or agents that influence or regulate the growth of plants.

8. A composition according to claim 7, wherein the self-supporting carrier-free granulates comprise fungi of the genus Metarhizium.

9. A composition according to claim 8, wherein the self-supporting carrier-free granulates comprise fungi of *Metarhizium anisopliae* strain P 0001, which has the deposit number DSM 3884, or strain P 0003, which has the deposit number DSM 3885, or mutants of said strains having the essential features and properties of P 0001 or P 0003.

10. A method of combatting insects comprising applying to such insects or to an insect habitat an insecticidally effective amount of the composition according to claim 7.

11. A method according to claim 10, wherein the self-supporting carrier-free granulates comprise fungi of the genus Metarhizium.

12. A method according to claim 11, wherein the self-supporting carrier-free granulates comprise fungi of *Metarhizium anisopliae* strain P 0001, which has the deposit number DSM 3884, or strain P 0003, which has the deposit number DSM 3885, or mutants of said strains having the essential features and properties of P 0001 or P 0003.

13. A composition comprising:
(a) self-supporting carrier-free granulates according to claim 1; in admixture with:
(b) nutrients, polyalcohols, non-toxic anti-oxidant substances or hygroscopic substances.

14. A composition according to claim 13, wherein the self-supporting carrier-free granulates comprise fungi of the genus Metarhizium.

15. A composition according to claim 14, wherein the self-supporting carrier-free granulates comprise fungi of *Metarhizium anisopliae* strain P 0001, which has the deposit number DSM 3884, or strain P 0003, which has the deposit number DSM 3885, or mutants of said strains having the essential features and properties of P 0001 or P 0003.

16. A method of combatting insects comprising applying to such insects or to an insect habitat an insecticidally effective amount of the composition according to claim 13.

17. A method according to claim 16, wherein the self-supporting carrier-free granulates comprise fungi of *Metarhizium anisopliae* strain P 0001, which has the deposit number DSM 3884, or strain P 0003, which has the deposit number DSM 3885, or mutants of said strains having the essential features and properties of P 0001 or P 0003.

18. A process for the preparation of self-supporting carrier-free granulates according to claim 1, said process comprising the following steps:
(A) initiating microorganism cell aggregation by either of steps (i), (ii) or (iii):
  (i) adding a detergent to an aqueous slurry of microorganism cells having an essentially hydrophobic cell surface, and introducing the suspended microorganism cells into water or an aqueous nutrient medium so that cell aggregation takes place; or
  (ii) adding acids or bases to a slurry of microorganism cells lacking an essentially hydrophobic cell surface, said microorganism cells in water or an aqueous nutrient medium, to adjust the pH value so that cell aggregation takes place; or
  (iii) adding a flocculant to a slurry or suspension of microorganism cells, said microorganism cells in water or a nutrient medium, so that cell aggregation takes place;
and subsequently:
(B) subjecting the resulting cell aggregates to fermentation under aerobic conditions in a nutrient medium until cell granulates form;
(C) separating off the cell granulates formed; and
(D) drying the separated cell granulates.

19. The process according to claim 18, further comprising subjecting the cell granulates separated in step (C) to incubation under the conditions of surface culture to form an essentially increased amount of permanent stages of microorganisms on the surface of the cell granulates.

20. The process according to claim 18, further comprising before step (D) adding nutrients, polyalcohols, non-toxic anti-oxidant substances or hygroscopic substances.

21. The process according to claim 18, further comprising before step (D) adding fungicides, insecticides, herbicides or agents that influence or regulate the growth of plants.

22. A process for the preparation of an agent for combating insects, which agent comprises a self-supporting carrier-free granulate of *Metarhizium anisopliae* comprising:
(A) initiating the cell aggregation by adding a non-ionic detergent (1.0% volume/volume) to an aqueous slurry of the microorganism, suspending the cells and introducing the cell suspension into water or an aqueous nutrient medium, and incubating the culture for 24 hours on a rotary shaker at 100 rpm and at 25° C. so that cell aggregation takes place;
(B) subjecting the resulting cell aggregates to fermentation under aerobic conditions in a nutrient medium until cell granulates form;
(C) separating off the cell granulates formed; and
(D) drying the separated cell granulates.

23. The process of claim 22 further comprising subjecting the cell granulates separated in step (C) to incubation under conditions of 100% relative atmospheric humidity at 25° C. for 60 to 70 hours to form an essentially increased amount of permanent stage conidia on the surface of the cell granulates.

24. The process according to claims 22 or 23 further comprising before step (D) adding nutrients, polyalcohols, non-toxic anti-oxidant substances or hygroscopic substances.

25. The process according claims 22 or 23, wherein the *Metarhizium anisopliae* is strain P 0001, which has the deposit number DSM 3884, or strain P 0003, which has the deposit number DSM 3885.

26. The process according claim 24, wherein the *Metarhizium anisopliae* is strain P 0001, which has the deposit number DSM 3884, or strain P 0003, which has the deposit number DSM 3885.

27. *Metarhizium anisopliae* strain P 0001, which has the deposit number DSM 3884, or strain P 0003, which has the deposit number DSM 3885.

28. Self-supporting carrier-free cell granulates according to claim 3, which comprise granulates of fungi of *Metarhizium anisopliae* strain P 0001, which has the deposit number DSM 3884, or strain P 0003, which has the deposit number DSM 3885.

29. A method according to claim 6, wherein the self-supporting carrier-free granulates comprise granulates of fungi of *Metarhizium anisopliae* strain P 0001, which has the deposit number DSM 3884, or strain P 0003, which has the deposit number DSM 3885.

30. A composition according to claim 9, wherein the self-supporting carrier-free granulates comprise granulates of fungi of *Metarhizium anisopliae* strain P 0001, which has the deposit number DSM 3884, or strain P 0003, which has the deposit number DSM 3885.

31. A method according to claim 12, wherein the self-supporting carrier-free granulates comprise granulates of fungi of *Metarhizium anisopliae* strain P 0001, which has the deposit number DSM 3884, or strain P 0003, which has the deposit number DSM 3885.

32. A composition according to claim 15, wherein the self-supporting carrier-free granulates comprise granulates of fungi of *Metarhizium anisopliae* strain P 0001, which has the deposit number DSM 3884, or strain P 0003, which has the deposit number DSM 3885.

33. A method according to claim 16, wherein the self-supporting carrier-free granulates comprise fungi of the genus Metarhizium.

34. A method according to claim 17, wherein the self-supporting carrier-free granulates comprise granulates of fungi of *Metarhizium anisopliae* strain P 0001, which has the deposit number DSM 3884, or strain P 0003, which has the deposit number DSM 3885.

* * * * *

UNITED STATES PATENT AND TRADEMARK OFFICE
CERTIFICATE OF CORRECTION

PATENT NO. : 5,418,164
DATED : May 23, 1995
INVENTOR(S) : Andersch, et al.

It is certified that error appears in the above-indentified patent and that said Letters Patent is hereby corrected as shown below:

Col. 20, line 20    Delete " Metarhizium " and substitute
                    -- Metarhizium --

Col. 20, line 34    Delete " Metarhizium " and substitute
                    -- Metarhizium --

Col. 20, line 49    Delete " Metarhizium " and substitute
                    -- Metarhizium --

Col. 20, line 63    Delete " Metarhizium " and substitute
                    -- Metarhizium --

Col. 21, line 10    Delete " Metarhizium " and substitute
                    -- Metarhizium --

Signed and Sealed this

Fifth Day of September, 1995

Attest:

BRUCE LEHMAN

*Attesting Officer*    *Commissioner of Patents and Trademarks*